United States Patent [19]

Wright et al.

[11] 4,115,407

[45] Sep. 19, 1978

[54] N-BENZYL-4-CHROMANAMINES

[75] Inventors: George C. Wright; Marvin M. Goldenberg, both of Norwich, N.Y.

[73] Assignee: Morton-Norwich Products, Inc., Norwich, N.Y.

[21] Appl. No.: 812,123

[22] Filed: Jul. 1, 1977

[51] Int. Cl.$^2$ .................... C07D 311/02; A61K 31/35
[52] U.S. Cl. .............................. 260/345.2; 260/345.5; 424/283
[58] Field of Search .......................... 260/345.2, 345.5

[56] References Cited

U.S. PATENT DOCUMENTS 2,903,454   9/1959   Richter et al. .................... 260/345.5

Primary Examiner—Nicky Chan
Attorney, Agent, or Firm—Anthony J. Franze

[57] ABSTRACT

Certain N-benzyl-4-chromanamines are useful as anti-inflammatory agents.

4 Claims, No Drawings

N-BENZYL-4-CHROMANAMINES

This invention is concerned with chemical compounds. More particularly, it is concerned with certain N-benzyl-4-chromanamines of the formula:

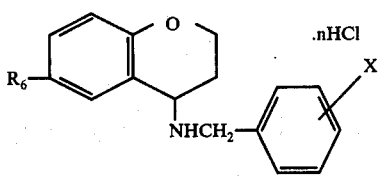

wherein $R_6$ is hydrogen or methoxy; X represents 3-amino, 4-amino or 2-amino-4,5-dimethoxy; and $n$ is 0 or 2.

The compounds of this invention possess pharmacological properties. Upon peroral administration to rats at a dose of about 300 mg/kg suitably formulated in a pharmaceutical dosage form such as a suspension, edema induced in rats by administration of carrageenin is suppressed [Winter et al. P.S.E.B.M. 111:554 (1962)].

These compounds can be formulated in various pharmaceutical dosage forms such as elixirs, tablets, capsules, suspensions and the like employing commonly used pharmaceutical carriers and excipients with which there is no incompatibility.

In order that this invention may be readily available to and understood by those skilled in the art, the following examples illustrate the currently preferred methods of preparing the compounds thereof.

EXAMPLE I

A. N-(m-Nitrobenzylidene)-4-chromanamine

An 80 g, (0.54 mole) portion of 4-chromanamine, and 650 ml of ethanol were placed in a 2-l, 3-necked flask, equipped with a stirrer and reflux condenser fitted with a drying tube. The slurry was treated with 85 g (0.56 mole) portion of m-nitrobenzaldehyde using rapid mechanical stirring. The reaction mixture was refluxed for 5 hrs., cooled 1 hr. and filtered. The yellow crystalline solid was washed with 100 ml of ethanol, ether, and dried, m.p. 117°–118°. Yield: 115 g (76%).

The product was recrystallized from 1.6l of ethanol, washed with 160 ml of ethanol, ether, and dried, m.p. 117°–118°. Yield: 98 g (65%).

Anal. Calcd. for $C_{16}H_{14}N_2O_3$: C, 68.07; H, 5.00; N, 9.93. Found: C, 68.06; H, 4.97; N, 9.94.

B. N-(m-Aminobenzyl)-4-chromanamine Dihydrochloride

A 57 g (0.20 mole) portion of A., 590 ml of ethanol and 5.4 g of 5% Pd/C (50% $H_2O$) were placed in a 2-l pressure bottle, and subjected to hydrogenation at 35 psig. The hydrogen uptake was 55 lb. (theory:55 lb. at 27°) in 1 hr. The reduction mixture was filtered to remove the catalyst, adjusted to pH 2 with 130 ml of HCl (isopropanol) solution, refrigerated overnight and filtered. The cream-colored solid was washed with 80 ml of isopropanol, ether, and dried, m.p. 69°–75° dec. Yield: 42 g (65%).

The crude product was recrystallized from 220 ml of ethanol, washed with 50 ml of ethanol, ether, and dried; m.p. 170°–180° dec. Yield: 34 g (52%).

Anal. Calcd. for $C_{16}H_{18}N_2O.2HCl$: C, 58.72; H, 6.16; N, 8.56. Found: C, 58.93; H, 6.29; N, 8.44.

EXAMPLE II

N-(p-Aminobenzyl)-6-methoxy-4-chromanamine Dihydrochloride

A 50 g (0.16 mole) portion of 6-methoxy-N-(p-nitrobenzylidene)-4-chromanamine, 440 ml of ethanol and 3.3 g of 5% Pd/C (50% $H_2O$) were placed in a 1.8l pressure bottle and subjected to hydrogenation at 40 psig. The hydrogen uptake was 47 lbs. (theory: 44 lb. at 30°) in 0.4 hr. The reduction mixture was filtered to remove the catalyst, refrigerated overnight, and stripped of ethanol under reduced pressure. The viscous residue was taken up in 110 ml of isopropanol, treated with 70 ml of HCl (isopropanol) to pH 2, refrigerated overnight and filtered. The yellow crystalline solid was washed with 100 ml of isopropanol, ether and dried; m.p. 208°–224° dec. Yield: 49 g (86%).

The crude product was recrystallized from 1.1l of methanol (Darco), washed with methanol, ether and dried; m.p. 206°–210° dec. Yield: 10 g (18%).

A second crop of 13 g (23%), m.p. 205°–208° dec., and a third crop of 7 g (12%), m.p. 203°–207°, were obtained by subsequent concentrations of the mother liquors to one-half volume, refrigeration, and filtration.

Anal. Calcd. for $C_{17}H_{20}N_2O_2.2HCl$: C, 57.15; H, 6.21; N, 7.84. Found: C, 57.02; H, 6.40; N, 7.67.

EXAMPLE III

A. 6-Methoxy-4-chromanone Oxime

A solution of 140 g (2.02 mole) of hydroxylamine hydrochloride in 630 ml of water, contained in a 3-l Erlenmeyer flask, was treated with 560 ml of 10% NaOH, and a solution of 250 g (1.40 mole) of 6-methoxy-4-chromanone in 560 ml of ethanol, all with rapid stirring. The reaction mixture was heated to boiling over 15 min., and continued to boil for 5 min. The mixture was stirred rapidly at room temperature for 3 hrs., refrigerated overnight and filtered. A white crystalline solid was washed with 1-l of water and air dried for 3 days; m.p. 120°–121°, Yield: 266 g (99%).

B. 6-Methoxy-4-chromanamine Hydrochloride

A 123 g (0.64 mole) portion of 6-methoxy-4-chromanone oxime and 540 ml of ethanol were placed in a 1-l pressure bottle, along with 32 g (wet basis) of Raney nickel catalyst previously washed with ethanol to remove excess water. The mixture was subjected to hydrogenation at 49 psig. The hydrogen uptake was 90 lb. (theory:98 lb. at 27°) in 7 hrs. The reduction mixture was filtered, stripped under a water pump to one-third volume, treated with 113 ml of isopropanol-HCl, pH 2, refrigerated overnight, and filtered. The resultant white crystalline solid was washed with 100 ml of isopropanol, ether and dried; m.p. 223°–224°dec. Yield: 94 g (68%).

The crude product was recrystallized from 1.2l of ethanol washed with 120 ml of ethanol, 200 ml of ether, and dried; m.p. 220°–222° dec. Yield: 54 g (39%).

Anal. Calcd. for $C_{10}H_{13}NO_2.HCl$: C, 55.68; H, 6.54; N, 6.50. Found: C, 55.50; H, 6.52; N, 6.38.

C. 6-Methoxy-N-(6-nitroveratrylidene)-4-chromanamine

A 90 g (0.40 mole) portion of B., 830 ml of ethanol and 90 g (0.43 mole) of 6-nitroveratraldehyde were placed in a 3-l, 3-necked flask equipped with a stirrer and reflux condenser. The reaction mixture was refluxed for 3.8 hrs., stored overnight at room temperature and filtered. The yellow needles were washed with 250 ml of ethanol, ether and dried; m.p. 143°–145° corr. Yield: 125 g (84%).

D. N-(6-Aminoveratryl)-6-methoxy-4-chromanamine

An 80 g (0.22 mole) portion of 6-methoxy-N-(nitroveratrylidene)-4-chromanamine, 850 ml of ethanol and 8 g of 5% Pd/C (50% moisture) were placed in a 1.8l pressure bottle and subjected to hydrogenation at 50 psig. The hydrogen uptake was 55 lbs. (theory: 57 lbs. at 27°) in 24 hrs. (1). The reduction mixture was filtered, refrigerated over the weekend and filtered. The cream crystalline solid was washed with 90 ml of ethanol and dried; m.p. 90°–92° corr. Yield: 23 g (29%).

The product was recrystallized from 145 ml of isopropanol (Darco), washed with 20 ml of isopropanol and dried; m.p. 90°–91° corr. Yield: 19 g (25%).

Anal. Calcd. for $C_{19}H_{24}N_2O_4$: C, 66.26; H, 7.04; N, 8.13. Found: C, 66.41; H, 7.04; N, 8.13.

What is claimed is:

1. A compound of the formula:

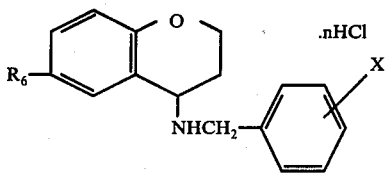

wherein $R_6$ is hydrogen or methoxy, $X$ represents 3-aminio, 4-amino or 2-amino-4,5-dimethyoxy; and $n$ is 0 or 2.

2. The compound N-(3-aminobenzyl)-4-chromanamine dihydrochloride.

3. The compound 6-methoxy-N-(4-aminobenzyl)-4-chromanamine dihydrochloride.

4. The compound 6-methoxy-N-(6-amino-veratryl)-4-chromanamine.